US009493538B2

(12) United States Patent
Finberg et al.

(10) Patent No.: US 9,493,538 B2
(45) Date of Patent: Nov. 15, 2016

(54) SNARES FOR PATHOGENIC OR INFECTIOUS AGENTS AND USES RELATED THERETO

(75) Inventors: Robert W. Finberg, Sudbury, MA (US); Damon R. Asher, Holden, MA (US)

(73) Assignee: UNIVERSITY OF MASSACHUSETTS, Worcester, MA (US)

( * ) Notice: Subject to any disclaimer, the term of this patent is extended or adjusted under 35 U.S.C. 154(b) by 1903 days.

(21) Appl. No.: 11/139,272

(22) Filed: May 27, 2005

(65) Prior Publication Data

US 2006/0018912 A1    Jan. 26, 2006

Related U.S. Application Data

(60) Provisional application No. 60/575,149, filed on May 28, 2004, provisional application No. 60/661,991, filed on Mar. 11, 2005.

(51) Int. Cl.

| C07K 16/46 | (2006.01) |
|---|---|
| C07K 14/705 | (2006.01) |
| C07K 16/28 | (2006.01) |
| C07K 16/10 | (2006.01) |

(52) U.S. Cl.
CPC ......... *C07K 14/705* (2013.01); *C07K 16/1009* (2013.01)

(58) Field of Classification Search
CPC ............. C07K 16/46; C07K 1/10; C07K 16/1009; C07K 14/705; C07K 14/70525; C07K 16/2896; C07K 2317/54; C07K 2317/55; C07K 2317/56; C07K 2317/622; C07K 2319/32
USPC ............ 424/178.1, 192.1; 530/391.1, 388.22
See application file for complete search history.

(56) References Cited

U.S. PATENT DOCUMENTS

| 4,522,811 | A | 6/1985 | Eppstein et al. | |
|---|---|---|---|---|
| 4,672,044 | A | 6/1987 | Schreiber | |
| 5,212,071 | A | 5/1993 | Fearon et al. | |
| 5,470,570 | A | 11/1995 | Taylor et al. | |
| 5,487,890 | A | 1/1996 | Taylor et al. | |
| 5,585,089 | A | 12/1996 | Queen et al. | |
| 5,834,589 | A | 11/1998 | Meruelo et al. | |
| 5,840,585 | A * | 11/1998 | Rodkey et al. | 436/161 |
| 5,861,156 | A * | 1/1999 | George et al. | 424/135.1 |
| 5,879,679 | A | 3/1999 | Taylor et al. | |
| 5,914,112 | A | 6/1999 | Bednar et al. | |
| 6,316,604 | B1 | 11/2001 | Fearon et al. | |
| 6,365,156 | B1 | 4/2002 | Lee | |
| 6,458,360 | B1 * | 10/2002 | Fearon et al. | 424/195.11 |
| 2002/0099000 | A1 * | 7/2002 | Muzykantov et al. | 514/2 |
| 2003/0219408 | A1 * | 11/2003 | Sabbadini et al. | 424/93.2 |
| 2003/0232045 | A1 * | 12/2003 | Ramberg et al. | 424/130.1 |
| 2004/0033232 | A1 * | 2/2004 | Ramberg et al. | 424/178.1 |
| 2004/0033584 | A1 * | 2/2004 | Lederberg | 435/235.1 |
| 2007/0224196 | A1 * | 9/2007 | Himawan et al. | 424/144.1 |

FOREIGN PATENT DOCUMENTS

| WO | WO89/01813 | * | 3/1989 |
|---|---|---|---|
| WO | WO 93/18160 | * | 9/1993 |
| WO | WO 02/46208 A2 | * | 6/2002 |

OTHER PUBLICATIONS

Taylor, R et al. J. Immunol. [1992] 148(8):2462-2468.*
Kimberly, RP et al. J. Clin. Invest. [1989] 84(3):962-970.*
Emlen, W et al. J. Immunol. Meth. [1990] 132(1):91-101.*
Yu et al., Investigative Ophthalmology & Visual Science 49(2): 522-527, Feb. 2008.*
Cochran et al., J. Immunol. Meth. 287: 147-158, 2004.*
Smith et al., Infection and Immunity 73(9): 5450-5457, 2005.*
Asher, Damon R. et al., "The erythrocyte viral trap: Transgenic expression of viral receptor on erythrocytes attenuates coxsackievirus B infection," *PNAS*, vol. 102(36):12897-12902 (2005).
Ferguson, P.J. et al., "Antigen-based heteropolymers. A potential therapy for binding and clearing autoantibodies via erythrocyte CR1," *Arthritis and Rheumatism*, vol. 38(2):190-200 (1995).
Lindorfer, Margaret A. et al., "A bispecific dsDNAXmonoclonal antibody construct for clearance of anti-dsDNA IgG in systemic lupus erythematosus," *Journal of Immunological Methods*, vol. 248:125-138 (2001).
Lindorfer, Margaret A. et al., "Heteropolymer-mediated clearance of immune complexes via erythrocyte CR1: mechanisms and applications," *Immunological Reviews*, vol. 183:10-24 (2001).
Taylor, R.P. et al., "Bispecific monoclonal antibody complexes facilitate erythrocyte binding and liver clearance okf a prototype particulate pathogen in a monkey model," *J. Immunol.*, vol. 159(8):4035-4044 (1997).
Taylor, R.P. et al., "Bispecific monoclonal antibody complexes bound to primate erythrocyte complement receptor 1 facilitate virus clearance in a monkey model," *J. Immunol.*, vol. 158(2):842-850 (1997).
Visvader, Jane E. et al., "Unsuspected role for the t-cell leukemia protein SCL/tal-1 in vascular development," *Genes and Development*, vol. 12:473-479 (1998).
Wilson, James G. et al., "Identification of a Restriction Fragment Length Polymorphism by a CR1 cDNA that Correlates with the Number of CR1 on Erythrocytes," *J. Exp. Med.*, vol. 164:50-59 (1986).
Yanagawa, Bobby et al., "Soluble Recombinant Coxsackievirus and Adenovirus Receptor Abrogates Coxsackievirus B3-Mediated Pancreatitis and Myocarditis in Mice," *The Journal of Infectious Diseases*, vol. 189:1431-1439 (2004).

* cited by examiner

*Primary Examiner* — Phuong Huynh
(74) *Attorney, Agent, or Firm* — Nelson Mullins Riley & Scarborough LLP; Amy E. Mandragouras, Esq.; Cynthia L. Kanik

(57) ABSTRACT

The present invention provides a snare molecules comprising an attachment moiety (which facilitates attachment of a receptor to a cell) and a receptor for a toxic pathogenic or infectious agent, e.g., a virus. Methods of producing such snare molecules and their therapeutic and/or prophylactic uses are also provided by the present invention.

13 Claims, 3 Drawing Sheets

SNARES FOR PATHOGENIC OR INFECTIOUS AGENTS AND USES RELATED THERETO

RELATED APPLICATIONS

This application claims the benefit of priority to U.S. Provisional Application Ser. No. 60/575,149, filed May 28, 2004 and U.S. Provisional Application Ser. No. 60/661,991, filed Mar. 11, 2005. The entire contents of each of these applications is incorporated herein by this reference.

BACKGROUND OF THE INVENTION

Primate erythrocytes, or red blood cells (RBC's), play an essential role in the clearance of antigens from the circulatory system. The formation of an immune complex in the circulatory system activates the complement factor C3b in primates and leads to the binding of C3b to the immune complex. The C3b/immune complex then binds to the type 1 complement receptor (CR1), a C3b receptor, expressed on the surface of erythrocytes via the C3b molecule attached to the immune complex. The immune complex is then chaperoned by the erythrocyte to the reticuloendothelial system (RES) in the liver and spleen for neutralization. The RES cells, most notably the fixed-tissue macrophages in the liver called Kupffer cells, recognize the C3b/immune complex and break this complex from the RBC by severing the C3b receptor-RBC junction, producing a liberated erythrocyte and a C3b/immune complex which is then engulfed by the Kupffer cells and is completely destroyed within subcellular organelles of the Kupffer cells. This pathogen clearance process, however, is complement-dependent, i.e., confined to immune complexes recognized by the C3b receptor, and is ineffective in removing immune complexes which are not recognized by the C3b receptor.

Taylor et al. have discovered a complement independent method of removing pathogens from the circulatory system. Taylor et al. have shown that chemical crosslinking of a first monoclonal antibody (mAb) specific to a primate C3b receptor to a second monoclonal antibody specific to a pathogenic antigenic molecule creates a snare heteropolymeric antibody or snare heteropolymer (HP) which offers a mechanism for binding a pathogenic antigenic molecule to a primate's C3b receptor without complement activation (U.S. Pat. Nos. 5,487,890; 5,470,570; and 5,879,679). It was also shown that 7B7, a monoclonal antibody to the bacteriophage ΦX174, was capable of partially neutralizing the bacteriophage when it was cross-linked and presented as an HP, although 7B7 had no neutralizing activity in its monomeric form. Taylor et al., J. of Immunology, 158:842-850 (1997). Taylor also reported an HP which can be used to remove a pathogenic antigen specific auto antibody from the circulation. Such an HP, also referred to as an "Antigen-based Heteropolymer" (AHP), contains a CR1 specific monoclonal antibody cross-linked to an antigen (see, e.g., U.S. Pat. No. 5,879,679; Lindorfer et al., 2001, Immunol Rev. 183: 10-24; Lindorfer et al., 2001, J. Immunol Methods 248: 125-138; Ferguson et al., 1995, Arthritis Rheum 38: 190-200). HPs have been shown to induce rapid clearance of targets from the bloodstream. However, HPs are rapidly cleared via their Fc regions, and consequently would not be expected to persist long enough in circulation to effectively capture virus that is continuously emerging from tissues. Furthermore, because HPs use an antibody to capture the pathogen, they are serotype specific and may be readily avoided by surface antigen mutation of pathogens.

Soluble receptors have also been developed to reduce infection in animals. For example, Coxsackievirus and adenovirus receptor (CAR) synthesized as a soluble IgG1-Fc fusion protein (CAF-Fc) has been found to reduce coxsackievirus B3-mediated pancreatitis and myocarditis in mice (Yanagawa et al. 2004. J. Infect. Dis. 189:1431). However, these soluble receptors may not be completely effective and seem to operate at low efficiency in vivo.

The development of compositions that have long half-lives in vivo and that can reduce infection of target cells by pathogenic agents would be of great benefit.

SUMMARY OF THE INVENTION

The present invention is based, at least in part, on the development of "snare" molecules which facilitate the binding of pathogenic or toxic agents to cells which are not naturally targets for the pathogenic agent (e.g., blood cells such as erythrocytes). The snare molecules comprise 1) an attachment moiety that facilitates attachment or expression of a receptor (e.g., a receptor for a toxic or pathogenic agent) by a cell which is not normally a target for the agent and 2) a binding moiety which is a receptor for the pathogenic or toxic agent. The non-target cells bound by the snare molecules compete for binding of the pathogenic or toxic agent with target cells bearing naturally occurring receptors and, thereby, reduce pathogenicity, toxicity, and/or infectiousness of the agent.

In one aspect, the invention pertains to a snare molecule, comprising an attachment moiety that facilitates attachment to a blood cell and a receptor for a pathogenic agent, wherein the receptor is not naturally found on the blood cell.

In one embodiment, the blood cell is an erythrocyte.

In one embodiment, the attachment moiety is an antibody that binds a cell surface molecule on a red blood cell.

In one embodiment, the antibody lacks an Fc portion.

In one embodiment, the antibody is a single chain antibody.

In one embodiment, the cell surface molecule on the erythrocyte is selected from the group consisting of: Fucosylglycoprotein alpha-n-acetylgalactosaminyltransferase, Complement C4, Aquaporin 1, Complement decay-accelerating factor, Band 3 anion transport protein, Duffy antigen, Glycophorin C, Galactoside 2-L-fucosyltransferase 1, Galactoside 2-L-fucosyltransferase 2, CD44, Kell blood group glycoprotein, Urea transporter, complement receptor 1, Membrane transport protein XK, Landsteiner-Wiener blood group glycoprotein, Galactoside 3(4)-L-fucosyltransferase, Lutheran blood group glycoprotein, Glycophorin A, Glycophorin B, Blood group RH(CE) polypeptide, Blood group RH(D) polypeptide, Xg glycoprotein, and Acetylcholinesterase.

In one embodiment, the cell surface molecule is CR1.

In one embodiment, the attachment moiety is a GPI anchor.

In one embodiment, the attachment moiety comprises a biotin molecule.

In one embodiment, the attachment moiety is a chemical crosslinking reagent.

In one embodiment, the blood cell is a human blood cell.

In one embodiment, the pathogenic agent is selected from the group consisting of: a bacterial cell, a virus, a toxin, and a parasite.

In one embodiment, the pathogenic agent is a virus.

In another aspect, the invention pertains to a composition comprising a snare molecule and a pharmaceutically acceptable carrier.

In another aspect, the invention pertains to a method of reducing the interaction of a pathogenic agent with its receptor on target host cells naturally infected by the pathogenic agent, comprising contacting non-target host cells lacking the naturally occurring receptor with a snare molecule comprising i) an attachment moiety that facilitates the binding or expression of a receptor by the non-target host cell and ii) a receptor for the pathogenic agent, such that interaction of the pathogenic agent with its naturally-occurring receptor on target host cells is reduced.

In one embodiment, the attachment moiety is an antibody.

In another embodiment, the attachment moiety is a GPI anchor.

In yet another embodiment, the attachment moiety comprises a biotin molecule.

In one embodiment, the attachment moiety is a chemical crosslinking reagent.

In another aspect, the invention pertains to a method of reducing the pathogenicity or infectiousness of a pathogenic agent comprising, contacting non-target host cells lacking the naturally occurring receptor with a molecule comprising i) an attachment moiety that facilitates the binding or expression of a receptor by the non-target host cell and ii) a receptor for the pathogenic agent, such that pathogenicity or infectiousness of a pathogenic agent is reduced.

In one embodiment, the attachment moiety is an antibody.

In one embodiment, the attachment moiety is a GPI anchor.

In one embodiment, the attachment moiety is a biotin molecule.

In one embodiment, the attachment moiety is a chemical crosslinking reagent.

DETAILED DESCRIPTION OF THE INVENTION

Figure 1:
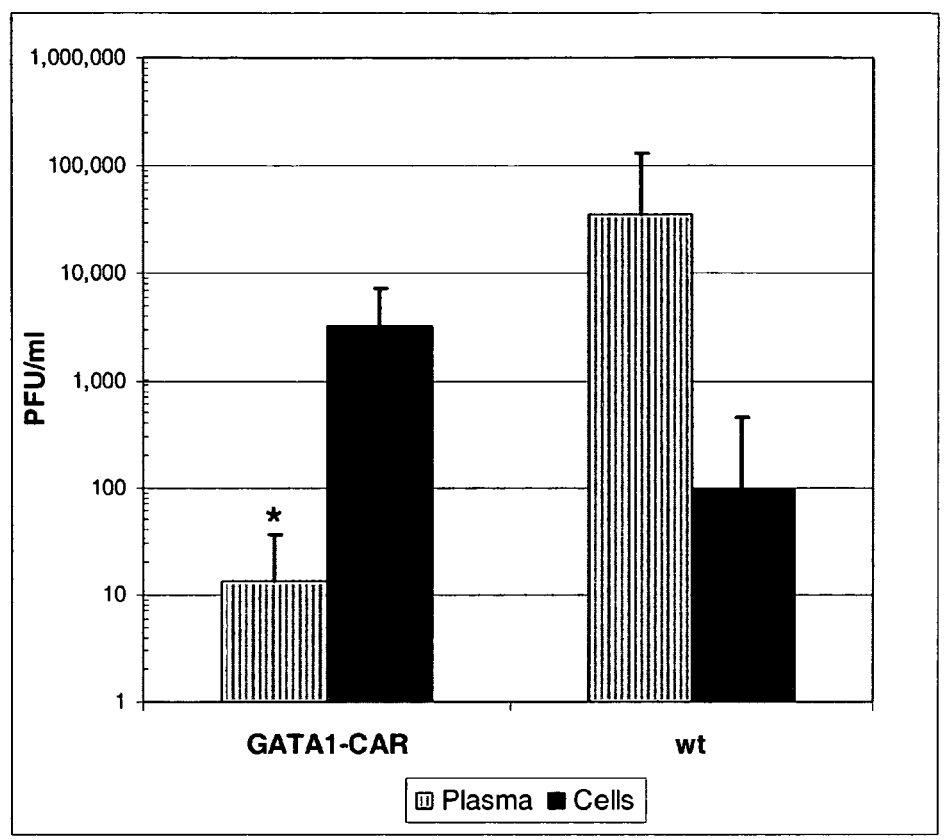
FIG. 1 shows reduction of viremia in GATA1-CAR mice. GATA1-CAR and wild type mice from the GATA1-CAR negative line were infected with CVB3 at $10^4$ PFU/mouse by intraperitoneal injection. Twenty-four hours later, blood was drawn and separated into cell and plasma fractions by centrifugation. The plaque forming units (PFU) in each of these fractions was quantitated by plaque assay on HeLa cells. Viral titers are presented as the geometric means of the groups (n=3) on a $\log_{10}$ scale. Standard errors and t-tests were based on the $\log_{10}$ transformed PFU data. The asterisk indicates a significant difference between the plasma CVB3 levels in the GATA1-CAR mice and the wt mice plasma ($p \leq 0.01$). The striped bars represent the plasma fraction and the solid bars the cell fraction.
Figure 2:
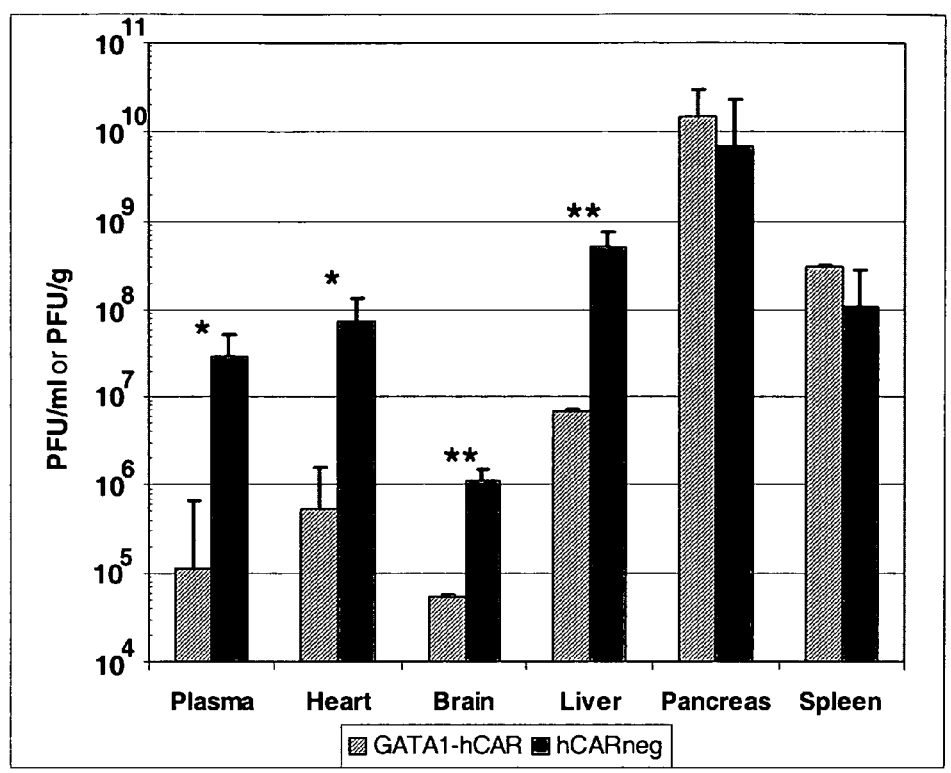
FIG. 2 shows viral titers in organs of GATA1-CAR mice. GATA1-CAR and wild type mice were infected with $10^3$ PFU CVB3/mouse by intraperitoneal injection. Three days later, blood and organs were harvested from the animals. The PFU in each of these tissues was quantitated by plaque assay on HeLa cells. Viral titers are presented as the geometric means of the groups on a $\log_{10}$ scale. Serum titers are presented as PFU/ml while the solid organs are PFU/g. Standard error and t-tests were based on the $\log_{10}$ transformed PFU data; p values were calculated to compare each hCAR-GATA1 organ to the same wt organ. Single asterisk: $0.1 < p \leq 0.5$; double asterisks: $p \leq 0.1$. The striped bars show GATA1-CAR mice and the solid bars show wild-type mice
Figure 3:
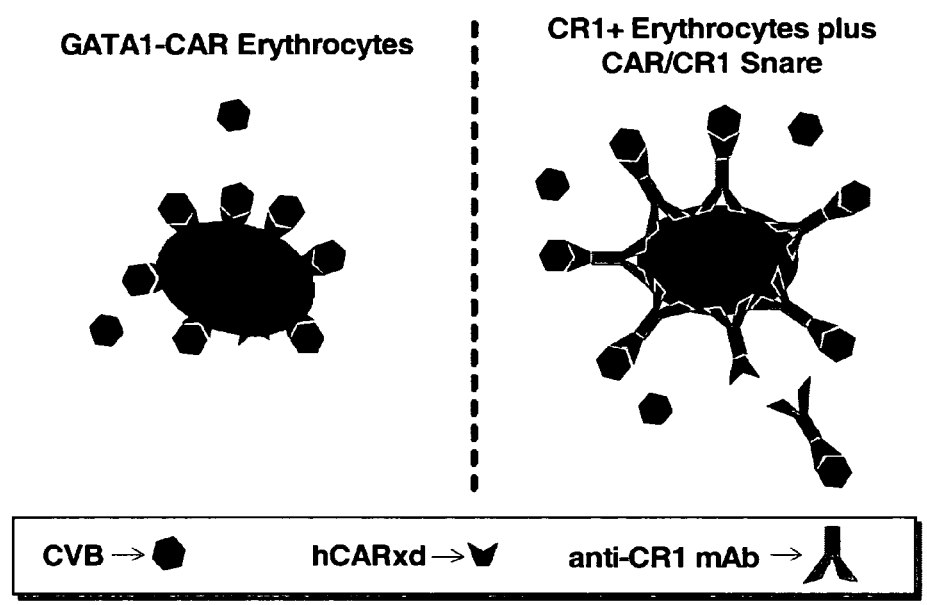
FIG. 3 shows a schematic of the replication of the reduction in viremia which would be afforded by the GATA1-CAR transgene using an injectable snare molecule, in this example, a "viral snare". In the schematic, the GATA1-CAR mouse reduces CVB viremia through a transgene that drives expression of hCAR on the surface on red blood cells. The viral snare consists of an antibody against hCR1 linked to a soluble CAR extracellular domain (CAR×d) molecule. Injected snare coats the surface of the erythrocytes of GATA1-hCR1 transgenic mice, creating red blood cells that present CAR. These blood cells bearing the snare should clear virus from the plasma as was shown for the GATA1-CAR erythrocytes.

The present invention provides snares molecules, which comprise an attachment moiety (e.g., an antibody or other agent) that facilitates attachment or expression (e.g. by binding to a molecule on the cell surface or by insertion to a cell membrane) on a cell (e.g., a blood cell such as an erythrocyte) linked to a receptor for a toxic or pathogenic agent (e.g., a pathogenic or opportunistic agent, such as a virus, bacteria, or parasite, or a toxin produced by such an agent (e.g., an exotoxin, enterotoxin, or endotoxin) or a chemical agent). The invention also provides methods of producing the snare molecules of the invention as well as therapeutic and prophylactic uses of the snare molecules of the invention.

In one embodiment, the snare molecule is a reagent that is a fusion of a recombinant form of a receptor for a pathogenic or toxic agent with an antibody specific for a cell surface antigen (e.g., a blood cell surface antigen, such as an erythrocyte surface antigen). In another embodiment, the attachment moiety (e.g., the antibody) and the receptor can be linked using a chemical cross linker rather than being expressed as a recombinant molecule.

In another embodiment, a snare molecule comprises a receptor for a pathogenic or toxic agent and a crosslinking reagent (e.g., a chemical crosslinker or a biotin/biotin-binding molecule or a biotin/biotin-binding molecule-biotin bridge) which links the receptor to the cell surface. In another embodiment, a snare molecule of the invention comprises a receptor for a pathogenic or toxic agent fused to a glycosylphosphatidylinositol (GPI) anchor for attachment to the cell surface.

The purpose of these or other such snare agents is to "coat" the cells with the receptor. These receptor-bearing cells would then act as decoy targets for the pathogenic agent and compete for binding with target cells in the host that bear naturally occurring pathogenic agent receptor molecules. For example a pathogenic agent binding to its receptor expressed on the erythrocyte surface would be unable to productively infect these cells. The cell bound virus would spend itself in a futile attempt to infect the cell and could also be cleared by resident macrophages in the liver and spleen.

One of the benefits of the snare approach of capturing pathogenic agents on the surface of cells, such as erythrocytes, using the receptor as bait is that it is expected that clearance of the pathogenic agent will be more efficient than that afforded by a neutralizing or opsonizing antibody. In contrast to a neutralizing antibody, the snare would not need to be present in a concentration high enough to extensively coat the pathogenic agent in order to be effective. Snares also do not require complement activation in order to utilize the endogenous erythrocyte-mediated clearance mechanisms. By directly binding the pathogenic or toxic agent to erythrocytes, the snare could allow exploitation of the reticuloendothelial system for antigen clearance in a more efficient manner than previously utilized reagents.

Another benefit to the snare approach is that, because the snare molecules use the cellular receptor to capture the pathogenic agents, variants of these agents, as long as they still bind to the receptor, would be bound by the snares. That is to say that, whereas antibodies may be limited to binding only a specific strain or serotype, snares would not be so limited. As an antigenic shift that would prevent binding to a cellular receptor would likely render any pathogenic agent noninfectious, snares could be administered against a broad range of strains or serotypes that share a cell surface receptor. In addition, the ability of an agent (e.g., a virus) to switch to an alternate receptor(s) could be compensated for through the use of cocktails of snares that include all known receptors to which the agent binds.

Before further description of the invention, certain terms are defined here.

I. Definitions

As used herein, the term "snare molecule" includes compounds comprising an attachment moiety that facilitates attachment or expression on a host cell (e.g. by binding to a molecule expressed by a cell, by insertion to a membrane, or by cross-linking) linked to a receptor for a pathogenic or toxic agent. A snare molecule of the invention can be made either in vitro or in vivo.

As used herein, the term "antibody" includes e.g., naturally occurring antibody or immunoglobulin molecules or genetically engineered antibody molecules that resemble naturally occurring antibody molecules. The term "antibody" as used herein also includes antigen binding fragments of antibody molecules, e.g., fab fragments, scfv molecules, minibodies, and the like.

As used herein the term "pathogen" or "pathogenic agent" includes microorganisms that are capable of infecting or parasitizing normal hosts (e.g., animals (such as mammals, preferably primates, e.g. humans)). As used herein, the term also includes opportunistic agents, e.g., microorganisms that are capable of infecting or parasitizing abnormal hosts, e.g., hosts in which normal flora have been supplanted, e.g., as a result of a treatment regimen, or immunocompromised hosts. As used herein the term also includes microorganisms whose replication is unwanted in a subject or toxic molecules (e.g., toxins) produced by microorganisms.

As used herein the term cell surface molecule includes molecules which are attached to the cell surface, e.g. that comprise extracellular domains.

As used herein, the term blood cell includes white blood cells and erythrocytes.

As used herein, the term "target host cells" includes cells of a host organism that bear receptor(s) for a pathogenic agent and which are naturally infected by the pathogenic agent.

As used herein, the term "non-target host cells" includes cells of an organism which do not naturally express a receptor, e.g., a receptor for a pathogenic agent and which are not naturally infected by the agent. In another embodiment, a cell which is less susceptible to the toxic effects of a pathogenic agent or a chemical agent can be used as a non-target host cell.

II. Components of Snare Molecules

The snares of the invention comprise an attachment moiety and a receptor to which a toxic agent, pathogen, pathogenic agent, or infectious agent binds. The snare molecules facilitate attachment or expression of the receptors on the surface of cells (e.g., non-target host cells such as blood cells, e.g., erythrocytes). In one embodiment, the cells are human cells. In another embodiment, the cells are cells of commercially important animals, such as livestock, domestic animals, or endangered animals. Exemplary attachment and receptor moieties are described further below.

A. Attachment Moieties

1. Antibodies to Cell Surface Molecules

In one embodiment, the snares of the invention comprise a receptor for a pathogenic or toxic agent or soluble form thereof coupled to a moiety that facilitates attachment to cells, such as erythrocytes.

In one embodiment, an antibody to a cell surface molecule can be used as the linking moiety that facilitates attachment to cells. The antibody can be directed to a molecule expressed on the surface of the target cell. Preferably, the molecule is preferentially expressed on erythrocytes. In one embodiment, the molecule is exclusively expressed on erythrocytes. In another embodiment, the molecule is displayed in clusters on the surface of erythrocytes.

Exemplary erythrocyte surface molecules (with Swiss Prot reference numbers) include: Fucosylglycoprotein alpha-n-acetylgalactosaminyltransferase (BGAT_HUMAN (P16442)), Complement C4 (CO4_HUMAN (P01028)), Aquaporin 1 (AQP1_HUMAN (P29972)), Complement decay-accelerating factor (Antigen CD55; DAF_HUMAN (P08174)), Band 3 anion transport protein (B3AT_HUMAN (P02730)), Duffy antigen (DUFF_HUMAN (Q16570)), Glycophorin C (GLPC_HUMAN (P04921)), Galactoside 2-L-fucosyltransferase 1 (FUT1_HUMAN (P19526)), Galactoside 2-L-fucosyltransferase 2 (FUT2_HUMAN (Q10981)), CD44 (CD44_HUMAN (P16070)), Kell blood group glycoprotein (KELL_HUMAN (P23276)), Urea transporter (UT1_HUMAN (Q13336)), complement receptor 1 (CR1_HUMAN (P17927)), Membrane transport protein XK (XK_HUMAN (P51811)), Landsteiner-Wiener blood group glycoprotein (LW_HUMAN (Q14773)), Galactoside 3(4)-L-fucosyltransferase (FUT3_HUMAN (P21217)), Lutheran blood group glycoprotein (LU_HUMAN (P50895)), Glycophorin A (GLPA_HUMAN (P02724)), Glycophorin B (GLPB_HUMAN (P06028)), Blood group RH(CE) polypeptide (RHCE_HUMAN (P18577)), Blood group RH(D) polypeptide (RHD_HUMAN (Q02161)), Xg glycoprotein (XG_HUMAN (P55808)), Acetylcholinesterase (ACES_HUMAN (P22303)). Although human molecules are provided in this list, orthologs of these, or other molecules, could readily be substituted by one of ordinary skill in the art.

In a preferred embodiment, a snare molecule of the invention comprises a binding specificity that recognizes a C3b-like receptor. As used herein, the term "C3b-like receptor" refers to any mammalian circulatory molecule expressed on the surface of a mammalian blood cell, which has an analogous function to CR1 in that it binds to a molecule associated with an immune complex, which is then chaperoned by the blood cell to, e.g., a phagocytic cell for clearance. In a preferred embodiment, the snare molecule comprises a binding specificity for CR1.

Preferably, the antibody binds to human CR1 gene. The nucleotide sequence of the wild type human CR1 gene is known in the art and is described in, for example, Wilson J. G. et al, (1986) *J. Exp. Med.* 164:50-59, U.S. Pat. No. 6,316,604, and U.S. Pat. No. 5,212,071 the contents of which are incorporated herein by reference.

Different allotypes of CR1 have been described in the art. For example, such allotypes have also been described by Wong et al. 1986. *J. Exp. Med.* 164:1531; Wong et al. 1989. *J. Exp. Med.* 169:847. Other human CR1 sequences are known in the art and can be found e.g., at GenBank accession No. AF169970; J. Immunol. 151:6214(1993) or J. Biol. Chem. 265:974-980 (1990). Nucleic acid molecules encoding such allotypic forms of CR1 can also be used to make antibodies for use in the instant invention.

Antibodies against cell surface molecules can be made using art recognized techniques, such as those described herein, or can be purchased commercially.

The term "antibody" as used herein refers to immunoglobulin molecules or antigen binding portions thereof (e.g., Fab fragments, scFv molecules, diabodies, and other art recognized forms). Immunoglobulin molecules are encoded by genes which include the kappa, lambda, alpha, gamma, delta, epsilon and mu constant regions, as well as a myriad of immunoglobulin variable regions. Light chains are classified as either kappa or lambda. Light chains comprise a variable light ($V_L$) and a constant light ($C_L$) domain. Heavy chains are classified as gamma, mu, alpha, delta, or epsilon, which in turn define the immunoglobulin classes IgG, IgM, IgA, IgD and IgE, respectively. Heavy chains comprise variable heavy ($V_H$), constant heavy 1 ($C_H1$), hinge, constant heavy 2 ($C_H2$), and constant heavy 3 ($C_H3$) domains. The IgG heavy chains are further sub-classified based on their sequence variation, and the subclasses are designated IgG1, IgG2, IgG3 and IgG4.

Antibodies can be further broken down into two pairs of a light and heavy domain. The paired $V_L$ and $V_H$ domains each comprise a series of seven subdomains: framework region 1 (FR 1), complementarity determining region 1 (CDR1), framework region 2 (FR2), complementarity determining region 2 (CDR2), framework region 3 (FR3), complementarity determining region 3 (CDR3), framework region 4 (FR4) which constitute the antibody-antigen recognition domain.

In one embodiment, an antibody is a chimeric antibody. A chimeric antibody may be made by splicing the genes from a monoclonal antibody of appropriate antigen specificity together with genes from a second human antibody of appropriate biologic activity. More particularly, the chimeric antibody may be made by splicing the genes encoding the variable regions of an antibody together with the constant region genes from a second antibody molecule. This method is used in generating a humanized monoclonal antibody wherein the complementarity determining regions are mouse, and the framework regions are human thereby decreasing the likelihood of an immune response in human patients treated with the antibody (U.S. Pat. Nos. 4,816,567, 4,816,397, 5,693,762; 5,585,089; 5,565,332 and 5,821,337, each of which is incorporated herein by reference in its entirety).

An antibody suitable for use in the present invention may be obtained from natural sources or produced by hybridoma, recombinant or chemical synthetic methods, including modification of constant region functions by genetic engineering techniques (U.S. Pat. No. 5,624,821). The antibody of the present invention may be of any isotype.

An anti-CR1 mAb that binds a human C3b receptor can be produced by known methods. In one embodiment, anti-CR1 mAb, preferably an anti-CR1 IgG, can be prepared using standard hybridoma procedure known in the art (see,- for example, Kohler and Milstein, 1975, Nature 256:495 497; Hogg et al., 1984, Eur. J. Immunol. 14:236-243; O'Shea et al., 1985, J. Immunol. 134:2580-2587; Schreiber, U.S. Pat. No. 4,672,044). A suitable mouse is immunized with human CR1 which can be purified from human erythrocytes. The spleen cells obtained from the immunized mouse are fused with an immortal mouse myeloma cell line which results in a population of hybridoma cells, including a hybridoma that produces an anti-CR1 antibody. The hybridoma which produces the anti-CR1 antibody is then selected, or 'cloned', from the population of hybridomas using conventional techniques such as enzyme linked immunosorbent assays (ELISA). Hybridoma cell lines expressing anti-CR1 mAb can also be obtained from various sources, for example, the murine anti-CR1 mAb that binds human CR1 described in U.S. Pat. No. 4,672,044 is available as hybridoma cell line ATCC HB 8592 from the American Type Culture Collection (ATCC). The obtained hybridoma cells are grown and washed using standard methods known in the art. Anti-CR1 antibodies are then recovered from supernatants.

In other embodiments, nucleic acids encoding the heavy and light chains of an antibody, preferably an anti-CR1 IgG, are prepared from the hybridoma cell line by standard methods known in the art. As a non-limiting example, cDNAs encoding the heavy and light chains of the anti-CR1 IgG are prepared by priming mRNA using appropriate primers, followed by PCR amplification using appropriate forward and reverse primers. Any commercially available kits for cDNA synthesis can be used. The nucleic acids are used in the construction of expression vector(s). The expression vector(s) are transfected into a suitable host. Non-limiting examples include E. coli, yeast, insect cell, and mammalian systems, such as a Chinese hamster ovary cell line. Antibody production can be induced by standard method known in the art.

An antibody can be prepared by immunizing a suitable subject with the antigen or portion thereof which can be purified from human erythrocytes. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975, Nature 256:495-497), the human B cell hybridoma technique by Kozbor et al. (1983, Immunol. Today 4:72), the EBV-hybridoma technique by Cole et al. (1985, Monoclonal Antibodies and Cancer Therapy, Alan R. Liss, Inc., pp. 77-96) or trioma techniques. The technology for producing hybridomas is well known (see Current Protocols in Immunology, 1994, John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., 1975, Nature, 256:495, or may be made by recombinant DNA methods (U.S. Pat. No. 4,816,567). The term "monoclonal antibody" as used herein also indicates that the antibody is an immunoglobulin.

In the hybridoma method of generating monoclonal antibodies, a mouse or other appropriate host animal, such as a hamster, is immunized as hereinabove described to elicit lymphocytes that produce or are capable of producing antibodies that will specifically bind to the protein used for immunization (see, e.g., U.S. Pat. No. 5,914,112, which is incorporated herein by reference in its entirety.)

Alternatively, lymphocytes may be immunized in vitro. Lymphocytes are then fused with myeloma cells using a suitable fusing agent, such as polyethylene glycol, to form a hybridoma cell (Goding, Monoclonal Antibodies: Principles and Practice, pp. 59 103, Academic Press, 1986). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT deficient cells.

Preferred myeloma cells are those that fuse efficiently, support stable high level production of antibody by the selected antibody producing cells, and are sensitive to a medium such as HAT medium. Among these, preferred myeloma cell lines are murine myeloma lines, such as those derived from MOPC 21 and MPC 11 mouse tumors available from the Salk Institute Cell Distribution Center, San Diego, Calif. USA, and SP 2 cells available from the American Type Culture Collection, Rockville, Md. USA.

Human myeloma and mouse human heteromyeloma cell lines also have been described for the production of human monoclonal antibodies (Kozbor, 1984, J. Immunol., 133:3001; Brodeur et al., Monoclonal Antibody Production Techniques and Applications, pp. 51 63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme linked immuno-absorbent assay (ELISA). The binding affinity of the monoclonal antibody can, for example, be determined by the Scatchard analysis of Munson et al., 1980, Anal. Biochem., 107:220.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59 103 (Academic Press, 1986)). Suitable culture media for this purpose include, for example, D-MEM or RPMI 1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A Sepharose, hydroxylapatite chromatography, gel electrophoresis, dialysis, or affinity chromatography.

Alternative to preparing monoclonal antibody-secreting hybridomas, a monoclonal antibody directed against an antigen can be identified and isolated by screening a recombinant combinatorial immunoglobulin library (e.g., an antibody phage display library) with human CR1. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

In addition, techniques developed for the production of "chimeric antibodies" (Morrison et al., 1984, Proc. Natl. Acad. Sci., 81, 6851-6855; Neuberger et al., 1984, Nature 312, 604-608; Takeda et al., 1985, Nature, 314, 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, each of which is incorporated herein by reference in its entirety)

Humanized antibodies are antibody molecules from non human species having one or more complementarity determining regions (CDRs) from the non human species and a framework region from a human immunoglobulin molecule. (see e.g., U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. Nos. 4,816,567 and 5,225,539; European Patent Application 125, 023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314: 446-449; Shaw et al., 1988, J. Natl. Cancer Inst. 80:1553-1559; Morrison 1985, Science 229:1202-1207; Oi et al., 1986, Bio/Techniques 4:214; Jones et al., 1986, Nature 321:552-525; Verhoeyan et al., 1988, Science 239:1534; and Beidler et al., 1988, J. Immunol. 141:4053-4060.

Complementarity determining region (CDR) grafting is another method of humanizing antibodies. It involves reshaping murine antibodies in order to transfer full antigen specificity and binding affinity to a human framework (Winter et al. U.S. Pat. No. 5,225,539). CDR grafted antibodies have been successfully constructed against various antigens, for example, antibodies against IL 2 receptor as described in Queen et al., 1989 (Proc. Natl. Acad. Sci. USA 86:10029); antibodies against cell surface receptors CAMPATH as described in Riechmann et al. (1988, Nature, 332:323; antibodies against hepatitis B in Cole et al. (1991, Proc. Natl. Acad. Sci. USA 88:2869); as well as against viral antigens respiratory syncitial virus in Tempest et al. (1991, Bio Technology 9:267). CDR grafted antibodies are generated in which the CDRs of the murine monoclonal antibody are grafted into a human antibody. Following grafting, most antibodies benefit from additional amino acid changes in the framework region to maintain affinity, presumably because framework residues are necessary to maintain CDR conformation, and some framework residues have been demonstrated to be part of the antigen binding site. However, in order to preserve the framework region so as not to introduce any antigenic site, the sequence is compared with established germline sequences followed by computer modeling.

A deimmunized antibody can also be used in the present invention. As used herein, the term "deimmunized antibody" refers to an antibody that is of a non-human origin but has been modified, i.e., with one or more amino acid substitutions, so that it is non-immunogenic or less immunogenic to a human when compared to the starting non-human antibody. In preferred embodiments, the deimmunized antibody comprises one or more non-human $V_H$ or $V_L$ sequences modified to comprise one or more amino acid substitutions so that the deimmunized antibody is non-immunogenic or less immunogenic to a human when compared to the respective unmodified non-human sequences (see WO 00/34317, WO 98/52976, and U.S. Provisional Application No. 60/458,869 filed on Mar. 28, 2003, all of which are incorporated herein by reference in their entirety). In a preferred embodiment, the deimmunized antibody is 19E9.

Completely human antibodies are particularly desirable for therapeutic treatment of human patients. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140.

The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65 93). For a detailed discussion of this technology for producing human antibodies and human monoclonal antibodies and protocols for producing such antibodies, see e.g., U.S. Pat. Nos. 5,625,126; 5,633,425; 5,569,825; 5,661,016; and 5,545,806. In addition, companies such as Abgenix, Inc. (Freemont, Calif.; see, for example, U.S. Pat. No. 5,985,615) and Medarex, Inc. (Princeton, N.J.), can be engaged to provide human antibodies directed against human CR1 using technology similar to that described above.

Completely human antibodies which recognize and bind a selected epitope can also be generated using a technique referred to as "guided selection." In this approach a selected non human monoclonal antibody, e.g., a mouse antibody, is used to guide the selection of a completely human antibody recognizing the same epitope (Jespers et al., 1994, Bio/technology 12:899-903).

A pre-existing anti-CR1 antibody, including but not limited to 7G9, HB8592, 3D9, 57F, 1B4 (see, e.g., Talyor et al., U.S. Pat. No. 5,487,890, which is incorporated herein by reference in its entirety), can also be used. In a preferred embodiment, a hybridoma cell line secreting a high-affinity anti-CR1 monoclonal antibody, e.g., 7G9 (murine IgG2a, kappa), is used to generate a master cell bank (MCB). Preferably, the master cell bank is tested for mouse antibody production, mycoplasma and sterility. The anti-CR1 antibody is then produced and purified from ascites fluid. In another preferred embodiment, the anti-CR1 monoclonal antibody used for the production of the snare molecules is produced in vitro (hollow-fiber bioreactor) and purified under cGMP. Other techniques are known in the art.

In one embodiment, the antibody lacks an Fc portion.

In another embodiment, the antibody is a single chain antibody (scFv) which comprises a fusion polypeptide consisting of a variable domain of a light chain fused via a polypeptide linker to the variable domain of a heavy chain. Methods of making scFv molecules are well known in the art.

2. GPI Anchors

Glycosylphosphatidylinisotol (GPI) anchored proteins are membrane bound proteins found throughout the animal kingdom. GPI anchors consist of: 1) ethanolamine attached via amide linkage to C-terminus 2) phosphodiester linkage of ethanolamine to the C6 hydroxyl of a mannose unit and 3) a heterogeneous glycan moiety (oligosaccharide) linking the mannose to the inositol headgroup of the phosphatidylinositol.

GPI anchors are synthesized and linked to glycoproteins inside the ER lumen. GPI anchor structures, because they are phospholipids, provide a high mobility of those cell surface proteins in the membrane.

Release of GPI anchored proteins can be accomplished by treatment with Phospholipase C, Phosphatidylinositolspecific (PLC-PI) (Available commercially, e.g., from Sigma Aldrich as Product Codes P 5542 and P 8804). The enzyme specifically hydrolyzes the phosphodiester bond of phosphatidylinositol to form a free 1,2-diacylglycerol and glycopeptide-bound inositol cyclic-1,2-phosphate.

GPI anchors can be added to proteins using techniques known in the art (see e.g., Premkumar et al. 2001 J. Biol. Chem. 82:234). Such methods can be used to add a GPI anchor to a receptor for a pathogenic or toxic agent to create a snare molecule of the invention.

3. Cross-linking Reagents

In one embodiment, biotin can be used to biotinylate cells (e.g., either in vitro or in vivo) using standard techniques. For example, 1.5 mg/ml sulfo-NHS—SS-biotin in PBS (phosphate-buffered saline plus 1 mM MgCl2 and 2.5 mM CaCl2) can be used in vitro to effect biotinylation of cells. This cell-impermeable reagent covalently conjugates biotin to primary amine groups of proteins, coupling the biotin to proteins via a reversible disulfide linkage.

This same reagent has also been used in vivo (see, e.g., Dale and Norenbert. 1990. *Biochim. Biophys. Acta* 1036:183 or Christian et al. 1993. *Blood.* 82:3469). For example in another study, two succinimide esters (biotin-N-hydroxy-succinimide ester [BNHS], caproylamidobiotin-N-hydroxy-succinimide ester [C-BNHS] have been used for biotin labeling of erythrocytes. When three doses of 1 mg C-BNHS were injected intravenously into mice at 24-h intervals, all the red cells were biotin labeled. Hoffmann-Fezer G., et al. 1991. *Ann Hematol.* 63:214-7.

Avidin, streptavidin and NeutrAvidin are biotin-binding proteins which each bind biotin with high affinity and selectivity. In one embodiment, a receptor for a toxic or pathogenic agent can be conjugated to a biotin-binding protein and then contacted with a biotinylated cell, either in vivo or in vitro, to form a snare molecule of the invention.

Avidin, streptavidin and NeutrAvidin biotin-binding protein each bind four biotins per molecule. The multiple binding sites for biotin on such molecules also permit a number of techniques in which avidin, streptavidin or NeutrAvidin can be used to bridge two biotinylated reagents. Thus, in another embodiment, this bridging method can be used to link biotin on the surface of a cell with a biotinylated receptor for a toxin or a pathogenic agent in the presence of a biotin-binding protein (either in vivo or in vitro) to form a snare molecule of the invention. This would allow specific conjugation and multimerization of biotinylated receptors on the cell surface using streptavadin.

In another embodiment, chemical cross-linking reagents can be used as attachment moieties. Polypeptides typically contain a variety of functional groups; e.g., carboxylic acid (COOH) or free amine (—NH.sub.2) groups, which are available for reaction with a suitable functional group on either the receptor or the antibody. Alternatively, polypeptides can be derivatized to attach additional reactive functional groups.

For example, in one embodiment, a bifunctional linker having one functional group reactive with a group on a receptor moiety and another group reactive with the cell can be used. Alternatively, derivatization can proceed through chemical treatment of the cell (e.g., a cell ex vivo) or the receptor moiety. For instance, chemical treatment of a glycoprotein involves glycol cleavage of the sugar moiety of a glycoprotein with periodate to generate free aldehyde groups. The free aldehyde groups on the glycoprotein may be reacted with free amine or hydrazine groups on an agent to bind the agent thereto (see, e.g., U.S. Pat. No. 4,671,958). In another example, free sulfhydryl groups can be generated on polypeptides (see, e.g., U.S. Pat. No. 4,659,839).

Heterobifunctional linkers, such as maleimide-hydroxysuccinimide ester or N-maleimido-6-aminocaproyl ester of 1-hydroxy-2-nitrobenzene-4-sulfonic acid can also be used as selective linkages (see, e.g., U.S. Pat. No. 5,851,527). Many other procedures and linker molecules for attachment of various compounds to proteins are known. See, for example, Coller et al. 1992. *J. Clin, Invest.* 89:546; European Patent Application No. 188,256; U.S. Pat. Nos. 4,671,958; 4,659,839; 4,414,148; 4,699,784; 4,680,338; 4,569,789; 5,856,571; 5,824,805; 5,470,997; 5,470,843; 5,470,932; 5,843,937 and 4,589,071; and Borlinghaus et al. Cancer Res. 47:4071-4075 (1987).

B. Receptors

The snare molecules of the invention also comprise a receptor for a pathogenic or toxic agent, e.g., in soluble form, for example lacking a transmembrane domain and, optionally, an intracellular domain. In another embodiment, a snare molecule comprisies a biologically active portion of such a receptor, i.e., ligand binding portion thereof.

In one embodiment, the receptor is a protein receptor. In another embodiment, the receptor is a carbohydrate receptor.

Exemplary pathogen receptors include: ICAM-1 (receptor for human rhinovirus); sialic acid (receptor for influenza A); vitronectin (receptor for adenovirus); CR2 (receptor for Epstein-Barr virus); heparin sulfate (receptor for HSV I and HSVII); poliovirus receptor (receptor for poliovirus); asialoglycoprotein (receptor for hepatitis B); CD4, CXCR4, CCR5 (receptors for HIV); CD81 (receptor for Hepatitis c virus; and CD14 and MD-2 (receptors for bacterial lipopolysaccharide (endotoxin)).

In one embodiment, the receptor is a soluble form of a receptor, e.g., a naturally occurring cell surface receptor that is modified in that it lacks a transmembrane domain. In one embodiment, the receptor is a fusion protein, e.g., comprising a soluble form of the receptor linked to a non-receptor polypeptide.

In one embodiment, the receptor is a receptor for a pathogen having a white blood cell target, such as HIV or EBV.

Other preferred receptors are those that recognize: hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Barr virus, human herpesvirus 6, cercopithecine herpes virus 1 (B virus), poxviruses or dengue virus.

In one embodiment, variants of naturally occurring receptor molecules can be made using art recognized techniques and used in the subject snare molecules provided that they retain the ability to bind the pathogen.

Methods for production of receptors for pathogenic agents or toxic agents are known in the art. Such receptors can be purified from cells or can be made using recombinant DNA technology. Methods of production of soluble forms of receptors which are normally transmembrane proteins are known in the art (see, for example, Smith et al. 1987. Science 238:1704; Fisher et al. 1988. Nature 331:76; Hussey et al. 1988. Nature 331:78; Deen et al. 1988. 331:82; Traunecker et al. 1988. Nature 331:84; Gershoni et al. 1988. PNAS 85:4087). Such methods are generally based on truncation of the nucleic acid molecule encoding the receptor protein to exclude the transmembrane portion, leaving intact the extracellular domain (or domains) capable of interacting with their specific ligands.

In one embodiment, the receptor portion of the snare molecule may comprise a fusion protein. For example, the pathogen binding moiety may optionally include a non-receptor polypeptide (e.g., an immunoglobulin Fc portion or modified form thereof) to promote solubility.

In one embodiment, the entire extracellular domain of the receptor may be included in the snare molecule. In another embodiment, where it is known in the art that only a portion of the extracellular domain is required for pathogen binding, the entire extracellular domain need not be included.

III. Production of Snare Molecules

Snare molecules of the invention can be produced either in vitro or in vivo. In addition, in embodiments where snare molecules are produced in vitro, they may be contacted with host cells either in vitro or in vivo. Cells that have been contacted with snare molecules of the invention can be infused into a subject (e.g., the same subject from which the cells were obtained or a histocompatable or blood group compatable subject) or the snare molecules can be directly administered into a subject's bloodstream.

For example, in one embodiment a snare molecule is prebound to hematopoietic cells ex vivo. For example, hematopoietic cells are collected from the individual to be treated (or alternatively hematopoietic cells from a non-autologous donor of the compatible blood type are collected) and incubated with an appropriate dose of the prophylactic or therapeutic snare molecule for a sufficient time so as to allow the snare molecule to bind to the surface of the cells. The cell/snare molecule mixture is then administered to the subject to be treated in an appropriate dose (see, for example, Taylor et al., U.S. Pat. No. 5,487,890).

In one embodiment, the cells are preferably hematopoietic cells, preferably blood cells, most preferably red blood cells.

Accordingly, in a specific embodiment, the invention provides a method of treating a mammal having an undesirable condition associated with the presence of a pathogenic or toxic molecule, comprising the step of administering a hematopoietic cell/snare molecule complex to the subject in an effective amount, the complex consisting essentially of a cell bound to one or more snare molecules. The method alternatively comprises a method of treating a mammal having an undesirable condition associated with the presence of a pathogenic antigenic molecule comprising the steps of (a) contacting a snare molecule with cells to form a hematopoietic cell/snare molecule complex; and (b) administering the cell/snare molecule complex to the mammal in an effective amount.

The invention also provides a method of making a cell/snare molecule complex comprising contacting a snare molecule with cells under conditions conducive to binding, such that a complex forms, the complex consisting essentially of a cell bound to one or more snare molecules.

Exemplary methods of making snare molecules are set forth below.

A. Recombinant Methods

Methods for the isolation and manipulation of recombinant DNA are routine. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

In general, the nucleic acid sequences encoding the components of a snare molecule (e.g. an antibody and a receptor) are obtained from cDNA and genomic DNA libraries or isolated using amplification techniques with oligonucleotide primers. To make a cDNA library, one should choose a source that is rich in the desired target mRNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, Gene 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180-182 (1977).

An alternative method of isolating nucleic acids encoding either part of the snare molecule combines the use of synthetic oligonucleotide primers and amplification of an RNA or DNA template (see U.S. Pat. Nos. 4,683,195 and 4,683,202; PCR Protocols: A Guide to Methods and Applications (Innis et al., eds., 1990)). Methods such as polymerase chain reaction (PCR) and ligase chain reaction (LCR) can be used to amplify nucleic acid sequences encoding fusion partners directly from mRNA, from cDNA, from genomic libraries or cDNA libraries. Oligonucleotides can be designed to amplify nucleic acids encoding known sequences.

Once the nucleic acid sequences encoding the two components of the snare molecule are isolated, they are readily fused to form a contiguous nucleic acid encoding the snare protein. Typically, the two components are amplified using amplification primers that incorporate a restriction enzyme site that affords the ability to cleave and ligate in the desired orientation (see, e.g., Ausubel et al., Current Protocols in Molecular Biology, Volumes 1-3, John Wiley & Sons, Inc. (1994-1998)).

In a preferred embodiment, the snare molecules of the invention are synthesized using recombinant nucleic acid techniques. After the gene encoding a viral-specific ligand/bacterial-specific ligand snare molecule is created, it is ligated into an expression cassette under the control of a particular promoter, expressing the protein in a host, isolating the expressed protein and, if required, renaturing the protein. Techniques sufficient to guide one of skill through such procedures are found in, e.g., Sambrook et al., Molecular Cloning—A Laboratory Manual, Cold Spring Harbor Laboratory, Cold Spring Harbor, N.Y., (1989) or Ausubel et al.

Finally, synthetic oligonucleotides can be used to construct recombinant genes for expression of protein of the snare molecules of this invention. Oligonucleotides can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

In particular, this method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the gene of interest. The specific subsequence is then ligated into an expression vector.

The sequence of the cloned genes and synthetic oligonucleotides can be verified after cloning using, e.g., the chain termination method for sequencing double-stranded templates of Wallace et al, Gene 16:21-26 (1981).

Once the desired gene is cloned, it is expressed to obtain the snare protein or its components. To obtain high level expression of a cloned gene, one typically subclones the gene of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site, as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding a component of the snare molecule or the snare molecule and signals required for efficient polyadenylation of the transcript, ribosome binding sites, and translation termination. A cleavable signal peptide sequence to promote secretion of the encoded protein by the transformed cell may be included in the construct. Additional elements of the cassette may include enhancers and, if genomic DNA is used as the structural gene, introns with functional splice donor and acceptor sites.

The elements that are typically included in expression vectors also include a replicon that functions in the host cell and can include a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical; any of the many resistance genes known in the art are suitable. The prokaryotic sequences are preferably chosen such that they do not interfere with the replication of the DNA in eukaryotic cells, if necessary.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra).

After the expression vector is introduced into the cells, the transfected cells are cultured under conditions favoring expression of the protein, which is recovered from the culture using standard techniques identified below.

B. Use of Cross-linking Reagents

In one embodiment, a snare molecule of the invention may comprise a cross-linking reagent as an attachment moiety. In another embodiment, a snare molecule of the invention may comprise a crosslinking reagent for linking an attachment moiety such as an antibody to a receptor for a pathogenic or toxic agent. Accordingly, in one embodiment, nucleic acid molecules encoding components of a snare molecule (antibodies (or antigen binding portions thereof) and receptor molecules), can be subjected to ligation and production as fusion molecules, whereas in another embodiment, these moieties can be bound together by chemical (covalent) conjugation or via non-covalent linkage (e.g., ionic interactions and hydrogen bonding).

In one embodiment of the invention, a receptor (e.g., in soluble form) is chemically conjugated (e.g., to the attachment moiety or directly to a cell) via covalent bonding. Means of chemically conjugating molecules are well known to those of skill. See, for instance, U.S. Pat. No. 5,856,125 for a discussion of means of conjugating molecules. The optimal procedure for attaching the receptor to the linking moiety or to the cell may vary according to the chemical structure of the receptor. Polypeptides typically contain a variety of functional groups; e.g., carboxylic acid (COOH) or free amine (—NH.sub.2) groups, which are available for reaction with a suitable functional group on either the receptor or the antibody. Alternatively, polypeptides can be derivatized to attach additional reactive functional groups.

In another embodiment, a "linking moiety", a molecule that is used to join the receptor to the attachment moiety (e.g., an antibody) is used. The linker is capable of forming covalent bonds to both the molecules. Suitable linkers are well known to those of skill in the art and include, but are not limited to, straight or branched-chain carbon linkers, heterocyclic carbon linkers, or peptide linkers. When the receptor and the antibody are both polypeptides, the linkers can be joined to the constituent amino acids through their side groups (e.g., through a disulfide linkage to cysteine), or to the alpha-carbon amino and carboxyl groups of the terminal amino acids.

In addition, a bifunctional linker having one functional group reactive with a group on one of the moieties to be joined and another group reactive with the other moiety can be used to form the desired conjugate. Alternatively, derivatization can proceed through chemical treatment of the receptor or the antibody. For instance, chemical treatment of a glycoprotein involves glycol cleavage of the sugar moiety of a glycoprotein with periodate to generate free aldehyde groups. The free aldehyde groups on the glycoprotein may be reacted with free amine or hydrazine groups on an agent to bind the agent thereto (see, e.g., U.S. Pat. No. 4,671,958). In another example, free sulfhydryl groups can be generated on polypeptides (see, e.g., U.S. Pat. No. 4,659,839).

Heterobifunctional linkers, such as maleimide-hydroxysuccinimide ester, can also be used as selective linkages (see, e.g., U.S. Pat. No. 5,851,527). Reaction of maleimide-hydroxysuccinimide ester with a receptor protein will derivatize amine groups on the protein, and the derivative can then be reacted with, e.g., the antibody with free sulfhydryl groups. Many other procedures and linker molecules for attachment of various compounds to proteins are known. See, for example, European Patent Application No. 188,256; U.S. Pat. Nos. 4,671,958; 4,659,839; 4,414,148; 4,699,784; 4,680,338; 4,569,789; 5,856,571; 5,824,805; 5,470,997; 5,470,843; 5,470,932; 5,843,937 and 4,589,071; and Borlinghaus et al. Cancer Res. 47:4071-4075 (1987).

C. Chemical Synthesis

When both the receptor and the attachment moiety (e.g., antibody) are relatively short proteins, a snare molecule is optionally synthesized as a single contiguous polypeptide using standard chemical peptide synthesis techniques. Alternatively, the receptor and the antibody can be synthesized separately, and then fused by condensation of the amino terminus of one molecule with the carboxyl terminus of the other molecule, thereby forming a peptide bond. In another alternative, the receptor and the antibody can each be condensed with one end of a peptide spacer molecule thereby forming a contiguous fusion protein.

Alternatively, fusion proteins can be produced by solid phase synthesis in which the C-terminal amino acid of the sequence is attached to an insoluble support followed by sequential addition of the remaining amino acids in the sequence. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A.; Merrifield, et al., J. Am. Chem. Soc., 85:2149-2156 (1963), and Stewart et al., Solid Phase Peptide Synthesis, 2nd ed. Pierce Chem. Co., Rockford, Ill. (1984) which are incorporated herein by reference.

While a receptor and an antibody are often joined directly together in a snare molecule, one of skill will appreciate that the molecules may be separated by a peptide spacer consisting of one or more amino acids. Generally, the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

D. Alternate Methods

Another possible method for synthesizing a snare molecule of the invention is to make a first snare molecule comprising e.g., an antibody directed against an epitope tag and an antibody specific for a molecule on the surface of a host cell. Then an epitope-tagged soluble pathogen receptor molecule can be synthesized and contacted with the epitope tagged molecule or cells that have been previously contacted with the epitope tagged molecule. The first snare molecule can be made using techniques known in the art Exemplary heteropolymers and antigen-based heteropolymers for testing in the instant invention and methods of making them are known in the art (for example as taught in WO 03007971A1; US 20020103343A1; U.S. Pat. Nos. 5,879,679; 5,487,890; 5,470,570; WO 9522977A1; WO/02075275A3, WO/0246208A2 or A3, WO/0180883A1, WO/0145669A1, WO 9205801A1, Lindorfer et al. 2001 *J. Immunol. Methods.* 248:125; Hahn et al. 2001. *J. Immnol.* 166:1057; Nardin et al. 1998. *J. Immunol. Methods.* 211:21; Kuhn et al. 1998. *J. Immunol.* 160:5088; Taylor et al. 1997. *Cancer Immunol. Immunother.* 45:152; Taylor et al. 1997. *J. Immunol.* 159: 4035; and Taylor et al. 1992. *J. Immunol.* 148:2462, U.S. Pat. No. 4,474,893; Staerz et al. (1985) *Nature* 314:628; Perez et al. (1985) *Nature* 316:354; Staerz and Bevan (1986) *Proc. Natl. Acad. Sci. USA,* 83:1453; and Staerz and Bevan (1986) *Immunol. Today* 7:241; U.S. Pat. No. 5,959,084; and U.S. Pat. No. 5,798,229) or as described above for the snare molecules of the invention.

IV. Purification and Testing of Snare Molecules

The snare molecules may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

In one embodiment, ion exchange chromatography can be performed using columns suitable for isolation of the snare molecules of the invention including DEAE, Hydroxylapatite, Calcium Phosphate (see generally Current Protocols in Immunology, 1994, John Wiley & Sons, Inc., New York, N.Y.).

In another embodiment, snare molecules are purified by two-step successive affinity chromatography (Corvalan and Smith, 1987, Cancer Immunol. Immunother., 24:127-132): the first column utilizes C3b-like receptor bound to a solid matrix which assays for C3b-like receptor binding via the anti-CR1 mAb portion of the snare molecule; and followed by a second column that utilizes specific binding of to the pathogen or antigenic portion thereof or an antibody which binds the receptor portion of the snare molecule.

Once expressed, a recombinant snare fusion proteins can be purified according to standard procedures, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)). Substantially pure compositions of about 50 to 95% homogeneity are preferred, and 80 to 95% or greater homogeneity are most preferred for use in the methods of the invention.

A number of procedures can be employed when recombinant fusions or fusion partners are purified. For example, proteins having established molecular adhesion properties can be reversibly fused to a snarec molecule. With the appropriate ligand, the snare molecule can be selectively adsorbed to a purification column and then freed from the column in a relatively pure form. The ligand is then removed by enzymatic activity. Finally the component of the snare molecule or the snare molecule could be purified using immunoaffinity columns.

In another embodiment, snare molecules can be made to comprise an epitope tag using methods known in the art. Exemplary epitope tags include beta Galactosidase, C-myc, E-tag, Flag, GFP, GST, HA, HSV, 6×HIS, Maltose Binding Protein, Protein C, S-tag, VSV-g, V5, and Biotin. The protein can then be purified using antibodies specific for the tag (which are commercially available) or other methods. For example, in the case of 6×His tags, nickel-coated agarose beads can be used for purification or in the case of GST tags, glutathione coated beads can be used for purification.

One of skill in the art will recognize that after chemical synthesis, biological expression and/or purification, the snare molecules of the invention may possess a conformation substantially different than the native conformations of the constituent polypeptides. In this case, it may be beneficial to denature and reduce the polypeptide and then to cause the polypeptide to re-fold into the preferred conformation. Methods of reducing and denaturing proteins and inducing re-folding are well known to those of skill in the art (see, e.g., Debinski, et al., J. Biol. Chem., 268:14065-14070 (1993); Kreitman and Pastan, Bioconjug. Chem., 4:581-585 (1993); and Buchner, et al., Anal. Biochem., 205:263-270 (1992)).

The activity of a snare molecule, e.g., whether it can inhibit the pathogenic effects or infectivity of a pathogen, can be tested by a method known in the art or using a transgenic mouse which expresses a human cell surface molecule, e.g., on its erythrocytes as described in U.S. Ser. No. 60/469,262, filed May 9, 2003.

V. Uses Of Snare Molecules

The snare molecules of the present invention are useful in treating or preventing a disease or disorder or any other undesirable condition associated with the presence of a pathogenic antigenic molecule.

Infectious diseases and/or symptoms associated with infection by a microbe are treated in a therapeutic method or prevented in a prophylactitc method by administration of a snare molecule of the invention.

In one embodiment, the invention pertains to a method of reducing the interaction of a pathogenic agent with its receptor on target host cells naturally infected by the pathogenic agent by contacting non-target host cells lacking the naturally occurring receptor with a snare molecule of the invention such that interaction of the pathogenic agent with its naturally-occurring receptor on target host cells is reduced.

In another embodiment, the invention pertains to a method of reducing the pathogenicity or infectiousness of a pathogenic agent by contacting non-target host cells lacking the naturally occurring receptor with a snare molecule of the invention such that pathogenicity or infectiousness of a pathogenic agent is reduced.

In one embodiment, snare molecules having more than one receptor specificity, i.e., a cocktail of snare molecules can be used. For example, in one embodiment, where a pathogen can bind to multiple receptors, snare molecules comprising all known receptors to which a pathogen binds can be used.

The preferred subject for administration of a snare molecule of the invention, for therapeutic or prophylactic purposes, is a mammal including but is not limited to non human animals (e.g., horses, cows, pigs, dogs, cats, sheep, goats, mice, rats, etc.), and in a preferred embodiment, is a human or non-human primate.

Exemplary diseases or disorders that can be treated or prevented by the use of a snare molecule of the present invention include, but are not limited to, those caused by pathogens such as hepatitis type A, hepatitis type B, hepatitis type C, influenza, varicella, adenovirus, herpes simplex type I (HSV I), herpes simplex type II (HSV II), rinderpest, rhinovirus, echovirus, rotavirus, respiratory syncytial virus, papilloma virus, papova virus, cytomegalovirus, echinovirus, arbovirus, hantavirus, coxsackie virus, mumps virus, measles virus, rubella virus, polio virus, human immunodeficiency virus type I (HIV I), and human immunodeficiency virus type II (HIV II), infection with any picornaviridae, enteroviruses, caliciviridae, any of the Norwalk group of viruses, togaviruses, such as alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein Barr virus, human herpesvirus 6, cercopithecine herpes virus 1 (B virus), pox viruses, Dengue virus, influenza virus, human respiratory syncytial virus, measles virus, herpes simplex virus, poliovirus, Newcastle virus, La Crosse virus, foot and mouth disease virus, and pseudorabies virus.

Other exemplary pathogens include: swine rotavirus, swine parvovirus, swine flu hemagglutinin, swine flu, hog colera virus, swine influenza virus, African swine fever virus, infectious bovine rhinotracheitis virus, infectious laryngotracheitis virus, neonatal calf diarrhea virus, Venezuelan equine encephalomyelitis virus punta toro virus, equine influenza virus, bovine respiratory syncytial virus or bovine parainfluenza virus, bovine respiratory syncytial virus, bovine parainfluenza virus, bovine viral diarrhea virus.

Bacterial diseases or disorders that can be treated or prevented by the use of snare molecules of the invention include, but are not limited to, *Mycobacteria, Rickettsia, Mycoplasma, Neisseria* spp. (e.g., *Neisseria meningitides* and *Neisseria gonorrhoeae*), *Legionella, Vibrio cholerae, Streptococci,* such as *Streptococcus pneumoniae, Staphylococcus aureus, Staphylococcus epidermidis, Pseudomonas aeruginosa, Corynobacteria diptheriae, Clostridium* spp., enterotoxigenic *Eschericia coli,* and *Bacillus anthracis* (anthrax), etc. Protozoal diseases or disorders that can be treated or prevented by the use of snare molecules of the present invention include, but are not limited to, *plasmodia, eimeria, Leishmania,* and *trypanosoma.*

In another embodiment, snare molecules of the invention can recognize a toxin produced by a microorganism. Exemplary toxins include, e.g., toxins produced by *Bacillus anthracis, Bacillus cereus, Bordatella pertussis, Clostridium botulinum, Clostridium perfringens, Clostridium tetani, Croynebacterium diptheriae, Salmonella* sp. *Shigella* sp., *Staphyloccus* sp., and *Vibrio cholerae.*

VI. Pharmaceutical Formulation and Administration

The snare molecules of the invention can be incorporated into pharmaceutical compositions suitable for administration. Such compositions typically comprise snare molecule and a pharmaceutically acceptable carrier. As used herein the language "pharmaceutically acceptable carrier" includes, e.g., solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the snare molecule, use thereof in the compositions is contemplated. Supplementary snare molecules can also be incorporated into the compositions.

A pharmaceutical composition of the invention is formulated to be compatible with its intended route of administration. The preferred route of administration is intravenous. Other examples of routes of administration include parenteral, intradermal, subcutaneous, transdermal (topical), and transmucosal. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that the viscosity is low and the snare molecule is injectable. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the snare molecule (e.g., one or more snare molecules) in the required amount in an appropriate solvent with one or a combination of ingredients enumerated above, as required, followed by filtered sterilization. Generally, dispersions are prepared by incorporating the snare molecule into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the snare molecules are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 which is incorporated herein by reference in its entirety.

It is advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of snare molecule calculated to produce the desired therapeutic effect in association with the required pharmaceutical carrier. The specification for the dosage unit forms of the invention are dictated by and directly dependent on the unique characteristics of the snare molecule and the particular therapeutic effect to be achieved, and the limitations inherent in the art of compounding such a snare molecule for the treatment of individuals.

The pharmaceutical compositions can be included in a kit, in a container, pack, or dispenser together with instructions for administration.

VII. Kits

The invention provides kits containing the snares, or components necessary to make the snares of the invention and instructions for use. Kits containing the pharmaceutical compositions of the invention are also provided.

This invention is further illustrated by the following examples which should not be construed as limiting. The contents of all references, patents and published patent applications cited throughout this application are incorporated herein by reference.

EXAMPLES

Example 1

Reduction in Pathogenesis of Coxsackievirus B3 in Mice Bearing Human Coxsackievirus and Adenovirus Receptor (CAR) on Erythrocytes Mice expressing human Coxsackievirus and Adenovirus Receptor (CAR) under the control of GATA1 were made. Briefly, an expression plasmid for the CAR gene was constructed. This fragment was inserted into the unique Not I site of plasmid pGATA-1, placing CAR under the transcriptional control of the erythroid specific promoter GATA1 (Visvader et al. *Genes Dev.* 12, 473-479). Orientation of the CAR gene was confirmed by sequencing. The vector was microinjected into fertilized oocytes harvested from F1 intercrosses of SJL×C57BL/6 mice. Following microinjection, the oocytes were implanted into pseudopregnant SW female mice. The resulting progeny were screened for integration of the transgene by PCR using mouse-tail DNA and flow cytometric analysis of erythrocytes for CAR expression. The mouse line was maintained by mating with C57BL/6 mice. In all experiments, CAR-negative littermates were used as wild-type controls. Mice were 10-14 weeks of age at the time of infection, with a roughly equal distribution of males and females.

The GATA1-CAR mice were infected with Coxsackievirus B3 (CVB3) in order to observe the effect of the transgene on pathogenesis of the virus. A group of GATA1-CAR mice and wildtype mice from the equally-backbred GATA1-hCAR negative line were inoculated intraperitoneally with CVB3 at $10^4$ PFU per mouse. Twenty-four hours later blood was drawn from the animals. The blood cells, consisting mainly of erythrocytes, were separated from the plasma by centrifugation and washed three times in phosphate buffered saline. The cell and plasma fractions were individually titrated for CVB3 by plaque forming unit assay. The absolute amount of virus in the plasma fraction was significantly reduced in the GATA1-CAR mice compared to wildtype (GATA1-CAR 1.13±0.43 vs. wt 4.55±0.56; $p \leq 0.01$, based on $\log_{10}$ transformed PFU/ml data) (FIG. 1). In the hCAR-expressing blood, a hundred-fold more virus was found in the cell fraction than in the plasma ($p<0.02$). The opposite arrangement was found in the wildtype blood controls, where there was more virus present in the plasma than on the cells ($p<0.05$).

The adherence of virus to the hCAR-expressing erythrocytes was accompanied by a reduction in viral penetration of some target organs. GATA1-CAR and wildtype mice were injected intraperitoneally with $10^3$ PFU CVB3 per mouse. Three days later, at the time of typical peak virus titer (e.g., Henke et al. 1995 J Virol. 69:6720-8), the mice were sacrificed and organs harvested. Viral titers were obtained for the plasma, heart, brain, liver, pancreas, and spleen (FIG. 2). The plasma titers again revealed a dramatic reduction in viremia in the GATA1-CAR mice. Significantly, the reduction in viremia was accompanied by a drop in the viral titers of several target organs. The virus was apparently unable to establish an infection in one GATA1-CAR mouse that showed no detectible virus in the blood or any organ by day 3. This mouse was excluded from calculations of the mean PFU values for the GATA1-CAR group. Among the remaining mice, there was a significant reduction in PFU of one to two logs in the plasma, heart, brain, and liver compared to the wildtype group. The heart and brain were similarly protected, albeit to a lesser degree, when the mice received a ten-fold greater initial inoculum of $10^4$ PFU/mouse. However, PFU in the spleen and pancreas were not decreased in the GATA1-CAR animals.

Example 2

GATA1-CAR Erythrocytes Bound and Neutralized Multiple CVB Serotypes

In vitro experiments established that CVB adhered to CAR expressed by GATA1-CAR erythrocytes, and that this interaction abolished viral infectivity. To test for receptor binding, CVB type 4 was incubated with blood or lymphocytes drawn from GATA1-CAR or wild-type mice. Anti-CVB4 monoclonal antibody (mAb) subsequently stained only GATA1-CAR erythrocytes, indicating that virus had adhered to the surface of these blood cells. Furthermore, exposure to the GATA1-CAR erythrocytes rendered multiple serotypes of the virus noninfectious. CVB3 incubated with GATA1-CAR erythrocytes rapidly lost infectivity, with a ten-fold reduction within 10 minutes and nearly complete neutralization by 1 hour. GATA1-CAR erythrocytes also curtailed CVB4 infectivity, albeit at a slower rate, achieving almost 90% inhibition by one hour. The level of CVB4 inhibition achieved by the CAR-expressing erythrocytes was ultimately equivalent to that of serotype-specific neutralizing mAb. This mAb was completely ineffective against CVB3. These experiments demonstrated that erythrocyte-expressed CAR matched the inhibitory potency of neutralizing antibody while maintaining the distinct advantage of being effective against multiple CVB serotypes.

Example 3

GATA1-CAR Erythrocytes Improved Survival of Infected Mice

Suppression of infection by erythrocyte-expressed CAR enabled GATA1-CAR mice to survive a CVB3 challenge that was invariably lethal to wild-type animals. A $4 \times 10^3$ PFU/mouse dose of CVB3 given to wild-type mice caused 50% mortality by day 5 post-infection and left no survivors by day 7. The GATA1-CAR mice were much more resilient, with no deaths before day 7 and 50% survival until the final time point at day 14. The mice that survived had resolved most outward signs of sickness such as altered posture, ruffled fur, and lethargy by the end of the experiment and maintained only a very low level of viremia (mean 350±300 PFU/ml whole blood).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A complex consisting essentially of a human erythrocyte bound to one or more bispecific molecules, wherein each bispecific molecule comprises an antibody or antigen binding fragment thereof which binds to human complement receptor 1 (CR1) on the cell surface of the human erythrocyte linked to a soluble form of a picornavirus receptor selected from the group consisting of a coxsackie-adenovirus receptor (CAR), a poliovirus receptor (PVR) and an intracellular adhesion molecule-1 (ICAM-1) that is not naturally found on the human erythrocyte, and wherein the complex binds to a picornavirus selected from the group consisting of a coxsackie virus, a poliovirus and a rhinovirus, and inhibits viremia and penetration of the picornavirus into organs.

2. A composition comprising the complex of claim 1 and a pharmaceutically acceptable carrier.

3. The complex of claim 1, wherein the antibody lacks an Fc portion.

4. The complex of claim 3, wherein the antibody is a single chain antibody.

5. A method of inhibiting viremia in a human subject comprising, administering an effective amount of a complex, the complex consisting essentially of a human erythrocyte bound to one or more bispecific molecules, wherein each of the bispecific molecules comprises an antibody or antigen binding fragment thereof which binds to human complement receptor 1 (CR1) on the cell surface of the erythrocyte linked to a soluble form of a picornavirus receptor selected from the group consisting of coxsackie-adenovirus receptor (CAR), poliovirus receptor (PVR) and intracellular adhesion molecule-1 (ICAM-1) that is not naturally found on the erythrocyte, and wherein the complex binds to a picornavirus selected from the group consisting of a coxsackie virus, a poliovirus and a rhinovirus, and inhibits viremia.

6. The complex of claim 5, wherein the picornavirus a coxsackie virus.

7. The complex of claim 1, wherein the picornavirus receptor is CAR.

8. A molecule comprising, (i) an antibody or antigen binding fragment thereof which binds to human complement receptor 1 (CR1) linked to (ii) a soluble form of a picornavirus receptor selected from the group consisting of selected from the group consisting of a coxsackie-adenovirus receptor (CAR), poliovirus receptor (PVR) and intracellular adhesion molecule-1 (ICAM-1) that is not naturally found on the erythrocyte, wherein the molecule inhibits viremia and viral penetration of target organs by binding a picornavirus selected from the group consisting of a coxsackie virus, a poliovirus and a rhinovirus, to erythrocytes.

9. The molecule of claim 8, wherein the molecule is a recombinant fusion protein comprising the antibody, or antigen binding fragment thereof, linked to the soluble picornavirus receptor.

10. The molecule of claim 8, wherein the antibody or antigen binding fragment thereof is chemically cross-linked to the soluble picornavirus receptor.

11. The molecule of claim 8, wherein the picornavirus is a coxsackie virus.

12. The molecule of claim 8, wherein the picornavirus receptor is a CAR receptor.

13. The complex of claim 1, wherein the picornavirus is a coxsackie virus.

* * * * *